United States Patent
Johnson et al.

(10) Patent No.: US 7,763,660 B2
(45) Date of Patent: Jul. 27, 2010

(54) **INHIBITORS OF *CANDIDA ALBICANS***

(75) Inventors: Douglas I. Johnson, Essex Junction, VT (US); Kurt A. Toenjes, Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 895 days.

(21) Appl. No.: 10/544,691

(22) PCT Filed: Feb. 5, 2004

(86) PCT No.: PCT/US2004/003208

§ 371 (c)(1),
(2), (4) Date: Feb. 15, 2006

(87) PCT Pub. No.: WO2004/071417

PCT Pub. Date: Aug. 26, 2004

(65) Prior Publication Data

US 2006/0154991 A1 Jul. 13, 2006

Related U.S. Application Data

(60) Provisional application No. 60/445,314, filed on Feb. 5, 2003.

(51) Int. Cl.
*A61K 31/138* (2006.01)
*A61P 31/00* (2006.01)
(52) U.S. Cl. ...................... 514/649; 514/406
(58) Field of Classification Search ................. 514/649, 514/406
See application file for complete search history.

(56) References Cited

U.S. PATENT DOCUMENTS

| | | | |
|---|---|---|---|
| 2,483,436 A | | 10/1949 | Rieveschl et al. |
| 2,963,401 A | * | 12/1960 | Davisson et al. ............ 424/121 |
| 3,257,412 A | * | 6/1966 | Baran ......................... 548/426 |
| 4,758,564 A | * | 7/1988 | Rentzea et al. ........... 514/239.2 |
| 4,873,265 A | | 10/1989 | Blackman |
| 4,883,792 A | | 11/1989 | Timmins et al. |
| 6,069,126 A | | 5/2000 | Abruzzo et al. |
| 6,174,882 B1 | | 1/2001 | Yelle |
| 6,468,997 B2 | | 10/2002 | Yelle |
| 7,067,315 B2 | * | 6/2006 | Westwood et al. .......... 435/342 |
| 2002/0099013 A1 | | 7/2002 | Piccariello et al. |
| 2002/0192300 A1 | | 12/2002 | Luo et al. |
| 2006/0194769 A1 | | 8/2006 | Johnson et al. |

FOREIGN PATENT DOCUMENTS

| | | | |
|---|---|---|---|
| WO | WO 9818927 | * | 5/1998 |
| WO | WO02095361 | * | 11/2002 |
| WO | WO 2004/071417 A2 | | 8/2004 |

OTHER PUBLICATIONS

Braun, B.R. et al., TUP1, CPH1 and EFG1 make independent contributions to filamentation in *Candida albicans*. Genetics. May 2000;155(1):57-67.
Brown, A.J. and Gow, N. A. Regulatory networks controlling *Candida albicans* morphogenesis. Trends Microbiol. Aug. 1999;7(8):333-8. Review.
Brown, A.J.P. In R.A. Calderone (ed.), *Candida* and Candidiasis. ASM Press, Washington, D.C. 87-93, 95-106, 2002.
Edmond, M.B. Nosocomial bloodstream infections in United States hospitals: a three-year analysis. Clin Infect Dis. Aug. 1999;29(2):239-44.
Filler, S.G. et al., Penetration and damage of endothelial cells by *Candida albicans*. Infect Immun. Mar. 1995;63(3):976-83.
Ibrahim, A.S. et al., Secreted aspartyl proteinases and interactions of *Candida albicans* with human endothelial cells. Infect Immun. Jun. 1998;66(6):3003-5.
Kao, R.Y.T. et al., A small-molecule inhibitor of the ribonucleolytic activity of human angiogenin that possesses antitumor activity. Proc Natl Acad Sci U S A. Jul. 23, 2002;99(15):10066-71. Epub Jul. 12, 2002.
Miller, M.G. et al., White-opaque switching in *Candida albicans* is controlled by mating-type locus homeodomain proteins and allows efficient mating. Cell. Aug. 9, 2002;110(3):293-302.
Mitchell, A.P. Curr. Opin. Microbiol. 1: 687-692, 1998.
Odds, F.C. Pathogenesis of *Candida* infections. J Am Acad Dermatol. Sep. 1994;31(3 Pt 2):S2-5. Review.
Schmidt-Westhausen, A. et al., Oral *Candida* and Enterobacteriaceae in HIV-1 infection: correlation with clinical candidiasis and antimycotic therapy. J Oral Pathol Med. Nov. 1991;20(10):467-72.
Scott, V.R. et al., New class of antifungal agents: jasplakinolide, a cyclodepsipeptide from the marine sponge, Jaspis species. Antimicrob Agents Chemother. Aug. 1988;32(8):1154-7.
Tsuchimori, N. et al., Reduced virulence of HWP1-deficient mutants of *Candida albicans* and their interactions with host cells. Infect Immun. Apr. 2000;68(4):1997-2002.
Ward, G.E. et al., Using small molecules to study big questions in cellular microbiology. Cell Microbiol. Aug. 2002;4(8):471-82. Review.
White, T.C. et al., Clin. Microbiol. Rev. 11: 382-402, 1998.
Akler et al., Use of fluconazole in the treatment of candidal endophthalmitis. Clin Infect Dis. Mar. 1995;20(3):657-64. Abstract Only.
Choi et al., Phosphorylation of p53, induction of Bax and activation of caspases during beta-lapachone-mediated apoptosis in human prostate epithelial cells. Int J Oncol. Dec. 2002;21(6):1293-9.

(Continued)

*Primary Examiner*—Sreeni Padmanabhan
*Assistant Examiner*—Sahar Javanmard
(74) *Attorney, Agent, or Firm*—Wolf, Greenfield & Sacks, P.C.

(57) ABSTRACT

The invention provides methods for identifying modulators of yeast phenotypic transitions and methods for treating fungal infections with modulators of phenotypic transitions of yeast cells. These methods include methods for identifying inhibitors of the budded-to-hyphal transition of *Candida albicans* and methods for treating fungal infections with inhibitors of the budded-to-hyphal transition of *Candida albicans*.

13 Claims, 3 Drawing Sheets

OTHER PUBLICATIONS

Chung et al., Involvement of calcium/calmodulin signaling in cercosporin toxin biosynthesis by *Cercospora nicotianae*. Appl Environ Microbiol. Feb. 2003;69(2):1187-96.

De Lucca et al., Antifungal peptides: novel therapeutic compounds against emerging pathogens. Antimicrob Agents Chemother. Jan. 1999;43(1):1-11.

Di Paolo et al., Manumycin inhibits *ras* signal transduction pathway and induces apoptosis in COLO320-DM human colon tumour cells. Br J Cancer. Feb. 2000;82(4):905-12.

Lee et al., An amino acid liquid synthetic medium for the development of mycelial and yeast forms of *Candida albicans*. Sabouraudia. Jul. 1975;13(2):148-53.

Lefler et al., Inhibition and killing of *Candida albicans* in vitro by five imidazoles in clinical use. Antimicrob Agents Chemother. Apr. 1984;25(4):450-4.

Luttrull et al., Treatment of ocular fungal infections with oral fluconazole. Am J Ophthalmol. Apr. 1995;119(4):477-81. Abstract Only.

Sehgal et al., Rapamycin (AY-22,989), a new antifungal antibiotic. II. Fermentation, isolation and characterization. J Antibiot (Tokyo). Oct. 1975;28(10):727-32. Abstract Only.

Tabekman et al., K252a, a Streptomyces toxin alkaloid, delays the experimental autoimmune encephalomyelitis (EAE) symptoms in SJL/J mice. Toxicon. 1995;33(3):289. Abstract Only.

Toenjes, K.A. et al., Small-molecule inhibitors of the budded-to-hyphal-form transition in the pathogenic yeast *Candida albicans*. Antimicrob Agents Chemother. Mar. 2005;49(3):963-72.

Troke et al., Efficacy of UK-49,858 (fluconazole) against *Candida albicans* experimental infections in mice. Antimicrob Agents Chemother. Dec. 1985;28(6):815-8.

Urbak et al., Fluconazole in the management of fungal ocular infections. Ophthalmologica. 1994;208(3):147-56. Abstract Only.

Wolff et al., Fluconazole vs low-dose amphotericin B for the prevention of fungal infections in patients undergoing bone marrow transplantation: a study of the North American Marrow Transplant Group. Bone Marrow Transplant. Apr. 2000;25(8):853-9.

\* cited by examiner

Figure 1: *C. albicans* morphological states

The budded or yeast-like (A), pseudohyphal (B), and hyphal growth forms are inter-convertible and differ in growth properties and cell cycle regulation. {Adapted from (12, 15)}

Figure 3.

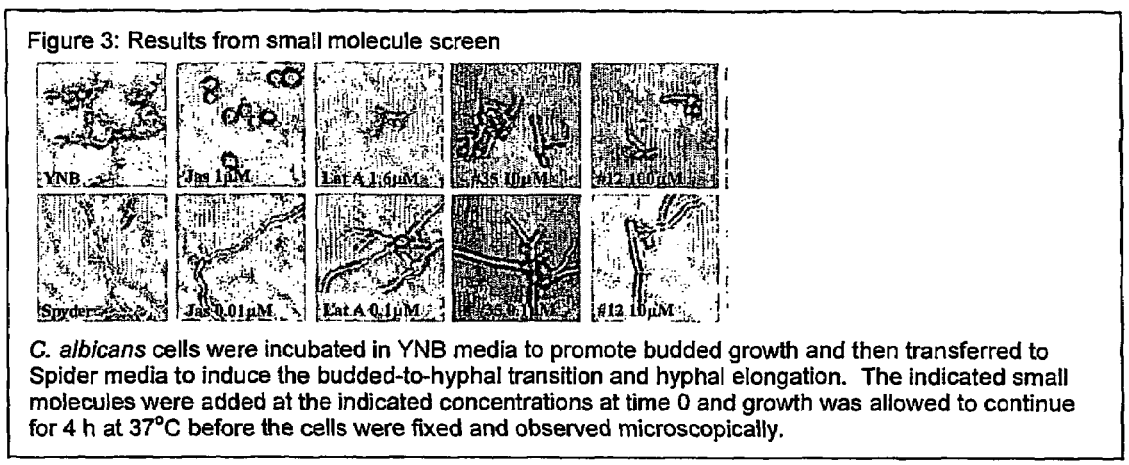

Figure 3: Results from small molecule screen

C. albicans cells were incubated in YNB media to promote budded growth and then transferred to Spider media to induce the budded-to-hyphal transition and hyphal elongation. The indicated small molecules were added at the indicated concentrations at time 0 and growth was allowed to continue for 4 h at 37°C before the cells were fixed and observed microscopically.

INHIBITORS OF *CANDIDA ALBICANS*

Related Applications

This application is a national stage filing under 35 U.S.C. § 371 of PCT International application PCT/US2004/003208, filed Feb. 5, 2004, which was published under PCT Article 21(2) in English, and claims the benefit under Title 35 U.S.C. §119(e) of U.S. provisional patent application Ser. No. 60/445,314, filed Feb. 5, 2003, entitled "Inhibitors of *Candida Albicans*".

FIELD OF THE INVENTION

The invention relates to methods for identifying modulators of yeast phenotypic transitions, including methods for identifying inhibitors of the budded-to-hyphal transition of *Candida albicans*. The invention also relates to treating fungal infections with modulators of phenotypic transitions of yeast cells, including inhibitors of the budded-to-hyphal transition of *Candida albicans*.

BACKGROUND OF THE INVENTION

*Candida albicans* is the most common and possibly the most important causative agent of human fungal infections (Edmond, M. B., et al. 1999, Clin. Infect. Dis. 29: 239-244). *Candida albicans*, (*C. albicans*) is a major opportunistic pathogen of immunocompromised hosts, including AIDS patients and patients undergoing chemotherapy, patients who have had tissue transplants, and patients with central venous catheters. Studies indicate that up to ninety percent of AIDS patients suffer from oropharyngeal and esophageal candidiasis, in which *C. albicans* is the major causative agent (Schmidt-Westhausen, A., et al., 1991, J. Oral Pathol. Med. 20: 467-472).

SUMMARY OF THE INVENTION

The invention is based, in part, on the discovery of a method of identifying inhibitors of the budded-to-hyphal transition of yeast cells, and the use of the inhibitors to treat fungal infections. Previously, most, if not all, antifungal agents killed yeast cells, and often were toxic to the host (patient) cells as well.

The present invention includes methods for treating fungal infections by administering a compound that modulates phenotypic transitions of yeast cells.

According to one aspect of the invention, methods for treating fungal infections by administering a compound of Formula I:

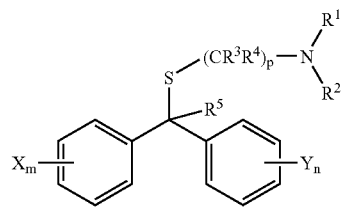

or a pharmaceutically acceptable salt thereof, are provided, wherein $R^1$ and $R^2$ are independently selected from the group consisting of hydrogen, $C_1$-$C_6$ alkyl, $C_1$-$C_6$ alkenyl, $C_1$-$C_6$ alkynyl, aryl, and heteroaryl; $R^3$, $R^4$, and $R^5$ are independently selected from the group consisting of hydrogen, hydroxy, halo, $C_1$-$C_6$ alkoxy, $C_1$-$C_6$ alkyl, $C_1$-$C_6$ alkenyl, and $C_1$-$C_6$ alkynyl; P is an integer varying from 1 to 5; each X and each Y are independently selected from the group consisting of halo, hydroxy, $C_1$-$C_6$ alkoxy, nitro, $C_1$-$C_6$ alkyl, $C_1$-$C_6$ alkenyl, $C_1$-$C_6$ alkynyl, amido, aryl, heteroaryl, and acyl; or two Xs or two Ys together form a 5, 6, or 7-membered ring; m is an integer varying from 0 to 5; and n is an integer varying from 0 to 5; in an effective amount.

In some embodiments, the compound is of the formula:

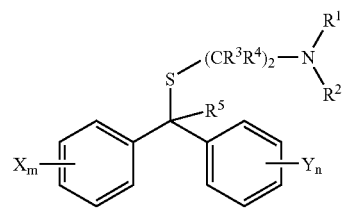

wherein $R^1$, $R^2$, $R^3$, $R^4$, $R^5$, $X_m$, and $Y_n$ are as defined above for Formula I. In other embodiments, the compound is of the formula:

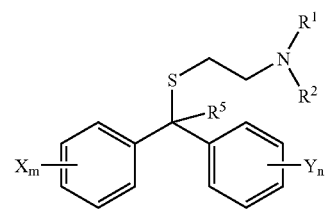

wherein $R^1$, $R^2$, $R^5$, $X_m$, and $Y_n$ are as described above for Formula I. In yet other embodiments, the compound has the formula:

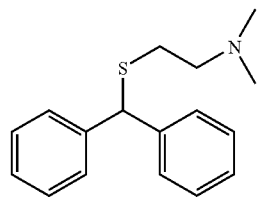

In some embodiments, the compounds above are provided as a mixture of isomers, which may include diastereomers or enantiomers. In other embodiments, the compound is greater than 60%, 70%, 80%, 90%, 95% or 99% of one isomer.

In another aspect of the invention, methods for treating a fungal infection by administering a compound of Formula II:

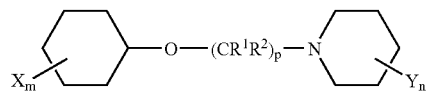

or a pharmaceutically acceptable salt thereof, are provided wherein $R^1$ and $R^2$ are independently selected from the group consisting of hydrogen, $C_1$-$C_6$ alkyl, $C_1$-$C_6$ alkoxy, hydroxy, and halo; p is an integer ranging from 1 to 5; each X and each Y are independently selected from the group consisting of halo, hydroxy, nitro, $C_1$-$C_6$ alkoxy, $C_1$-$C_6$ alkyl, $C_1$-$C_6$ alkenyl, $C_1$-$C_6$ alkynyl, amido, aryl, heteroaryl, and acyl; or two Xs or two Ys together form a 5, 6, or 7-membered ring; m is an integer varying from 0 to 11; and n is an integer varying from 0 to 11 in an effective amount.

In some embodiments, the compound is of the formula:

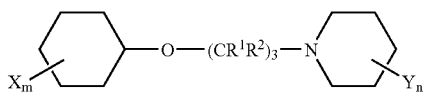

wherein $R^1$, $R^2$, $X_m$, $Y_n$ are as defined above for Formula II. In some embodiments, m is an integer greater than or equal to 2. In some embodiments, the compound is of the formula:

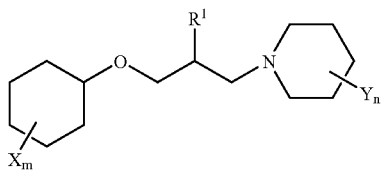

wherein $R^1$, $Y_m$, and $Y_n$ are as defined above for Formula II. In other embodiments, the compound is of the formula:

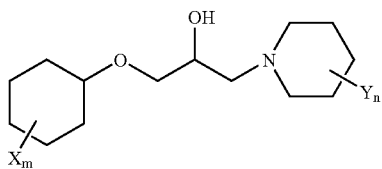

wherein $X_m$, and $Y_n$ are as described above for Formula II. In certain embodiments, X and Y are each $C_1$-$C_6$ alkyl. In one embodiment, the compound has the formula:

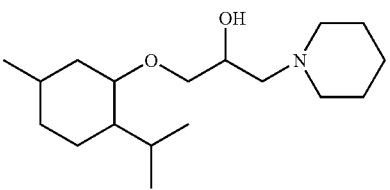

In another embodiment, the compound has the formula:

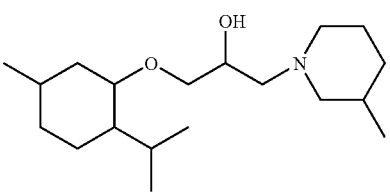

In some embodiments, the compounds above are provided as a mixture of isomers, which may include diastereomers or enantiomers. In other embodiments, the compound is greater than 60%, 70%, 80%, 90%, 95% or 99% of one isomer.

In another aspect of the invention, methods for treating fungal infections comprising administering a compound of Formula III:

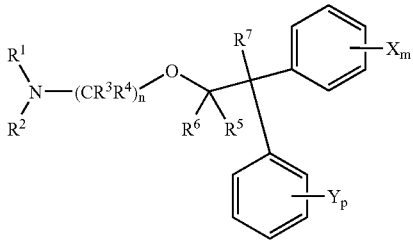

or a pharmaceutically acceptable salt thereof, are provided, wherein $R^1$ and $R^2$ are independently selected from the group consisting of hydrogen, $C_1$-$C_6$ alkyl, $C_1$-$C_6$ alkenyl, $C_1$-$C_6$ alkynyl, aryl, and heteroaryl; wherein $R^3$, $R^4$, $R^5$, $R^6$, and $R^7$ are independently selected from the group consisting of hydrogen, hydroxy, $C_1$-$C_6$ alkoxy, halo, $C_1$-$C_6$ alkyl, $C_1$-$C_6$ alkenyl, and $C_1$-$C_6$ alkynyl; or $R^5$ and $R^6$ together are a carbonyl oxygen; n is an integer ranging from 1 to 5; each X and each Y are independently selected from the group consisting of halo, hydroxy, $C_1$-$C_6$ alkoxy, nitro, $C_1$-$C_6$ alkyl, $C_1$-$C_6$ alkenyl, $C_1$-$C_6$ alkynyl, amido, aryl, heteroaryl, and acyl; or two Xs or two Ys together form a 5, 6, or 7-membered ring; m is an integer varying from 0 to 5; and p is an integer varying from 0 to 5 in an effective amount.

In some embodiments, n is 1 or 2. In another embodiment, n is 3. In yet other embodiments, n is 4 or 5. In some embodiments, m and p are each 0, that is the aryl rings are not substituted. In other embodiments, one or both of the aryl rings may be substituted.

In some embodiments, $R^5$ and $R^6$ together are a carbonyl oxygen. In some of these embodiments, the compounds are of the formula:

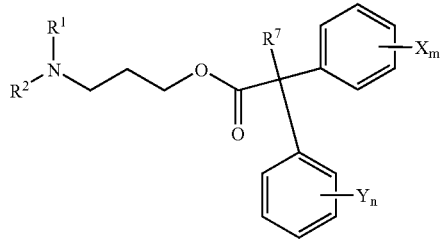

wherein $R^1$, $R^2$, $R^7$, $X_m$, and $Y_n$ are as described above for Formula III.

In some embodiments, $R^7$ is $C_1$-$C_6$ alkoxy and $R^1$ and $R^2$ are each alkyl. In some of these embodiments, the compound is of the formula:

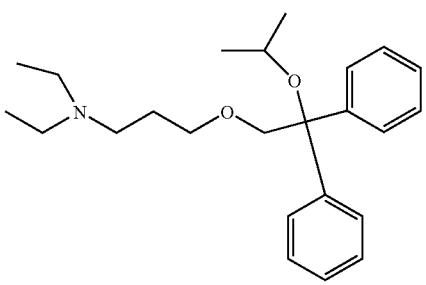

In some embodiments, the compounds above are provided as a mixture of isomers, which may include diastereomers or enantiomers. In other embodiments, the compound is greater than 60%, 70%, 80%, 90%, 95% or 99% of one isomer.

In another aspect of the invention, methods for treating fungal infections by administering compounds of Formula IV:

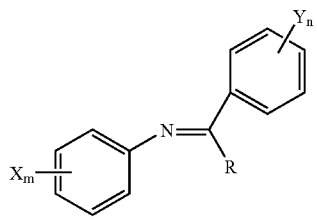

or a pharmaceutically acceptable salt thereof are provided, wherein R is selected from the group consisting of hydrogen, hydroxy, $C_1$-$C_6$ alkoxy, halo, $C_1$-$C_6$ alkyl, $C_1$-$C_6$ alkenyl, and $C_1$-$C_6$ alkynyl; each X and each Y are independently selected from the group consisting of halo, hydroxy, $C_1$-$C_6$ alkoxy, nitro, $C_1$-$C_6$ alkynyl, amido, aryl, heteroaryl, and acyl; or two Xs or two Ys together form a 5, 6, or 7-membered ring; m is an integer ranging from 0 to 5; and n is an integer ranging from 0 to 5 in an effective amount.

In some embodiments, R is hydrogen. In other embodiments, R is not hydrogen, and the compounds may exist only in the E or Z configuration, or a mixture thereof. In other embodiments, each X and each Y are selected from $C_1$-$C_6$ alkoxy and hydroxy. In some embodiments, n is 0. In other embodiments, n is 1, 2, 3, 4, or 5.

In still other embodiments, m is 0. In other embodiments, m is 1. In still other embodiments, m is 2, 3, 4, or 5. In one particular embodiment, the compound is:

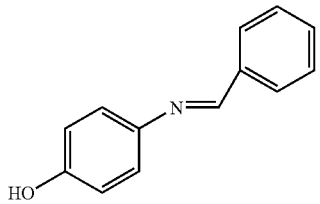

In some embodiments, the compounds above are provided as a mixture of isomers, which may include diastereomers or enantiomers. In other embodiments, the compound is greater than 60%, 70%, 80%, 90%, 95% or 99% of one isomer.

In another aspect of the invention, methods for treating fungal infections by administering a compound of Formula V:

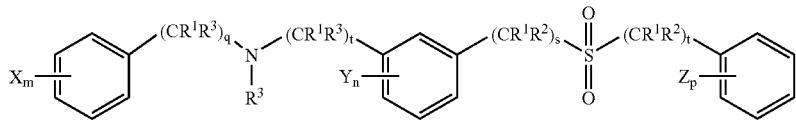

or a pharmaceutically acceptable salt thereof are provided, wherein each $R^1$, each $R^2$, and each $R^3$ are independently selected from the group consisting of hydrogen, hydroxy, $C_1$-$C_6$ alkoxy, halo, $C_1$-$C_6$ alkyl, $C_1$-$C_6$ alkenyl, and $C_1$-$C_6$ alkynyl; or $R^1$ and $R^2$ together are a carbonyl oxygen; each q is an integer ranging from 0 to 6; each r is an integer ranging from 0 to 6; each s is an integer ranging from 0 to 6; each t is an integer ranging from 0 to 6; each X, each Y, and each Z are independently selected from the group consisting of halo, hydroxy, $C_1$-$C_6$ alkoxy, nitro, $C_1$-$C_6$ alkynyl, amido, aryl, heteroaryl, and acyl; or two Xs or two Ys, or two Zs, together form a 5, 6, or 7-membered ring; m is an integer ranging from 0 to 5; n is an integer ranging from 0 to 4; and p is an integer ranging from 0 to 5 in an effective amount.

In some embodiments, each X, each Y, and each Z are selected from halo and $C_1$-$C_6$ alkoxy. In some embodiments, $R^3$ is hydrogen. In other embodiments, at least one $R^1$ and at least one $R^2$ together are a carbonyl oxygen.

In some embodiments, q is 1. In other embodiments, q is 0. In still other embodiments, q is 2, 3, 4, 5, or 6. In other embodiments, r is 0. In still other embodiments, r is 1, 2, 3, 4, 5, or 6. In some embodiments, s is 0. In other embodiments, s is 1, 2, 3, 4, 5, or 6. In some embodiments, t is 0. In other embodiments, t is 1, 2, 3, 4, 5, or 6. In a particular embodiment, the compound is:

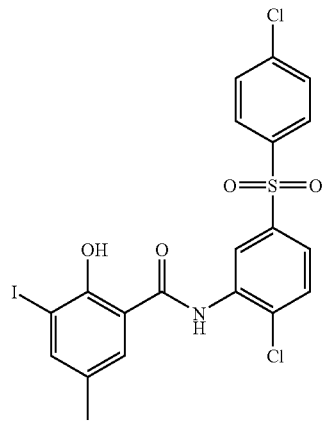

In some embodiments, the compounds above are provided as a mixture of isomers, which may include diastereomers or enantiomers. In other embodiments, the compound is greater than 60%, 70%, 80%, 90%, 95% or 99% of one isomer.

In another aspect of the invention, methods for treating fungal infections by administering compounds of Formula VI:

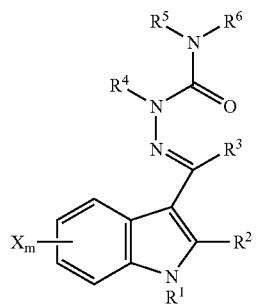

or a pharmaceutically acceptable salt thereof are provided, wherein $R^1$, $R^4$, $R^5$ and $R^6$ are each independently selected from the group consisting of hydrogen, $C_1$-$C_6$ alkyl, $C_1$-$C_6$ alkenyl, and $C_1$-$C_6$ alkynyl; $R^2$ and $R^3$ are each independently selected from the group consisting of hydrogen, hydroxy, $C_1$-$C_6$ alkoxy, halo, $C_1$-$C_6$ alkyl, $C_1$-$C_6$ alkenyl, and $C_1$-$C_6$ alkynyl; each X is independently selected from the group consisting of halo, hydroxy, $C_1$-$C_6$ alkoxy, nitro, $C_1$-$C_6$ alkynyl, amido, aryl, heteroaryl, and acyl; and m is an integer ranging from 0 to 4; in an effective amount.

In some embodiments, $R^1$ is hydrogen. In other embodiments, $R^2$ is hydrogen. In another embodiment, $R^4$ is hydrogen. In yet other embodiments, one or both of $R^5$ and $R^6$ are hydrogen. In preferred embodiments, at least one of $R^1$, $R^2$, $R^3$, $R^4$, $R^5$ and $R^6$ is not hydrogen. In some embodiments, m is 0. In other embodiments, m is 1. In still other embodiments, m is 2, 3, or 4.

In some embodiments, the compounds above are provided as a mixture of isomers, which may include diastereomers or enantiomers. In other embodiments, the compound is greater than 60%, 70%, 80%, 90%, 95% or 99% of one isomer.

In one particular embodiment, the compound is other than:

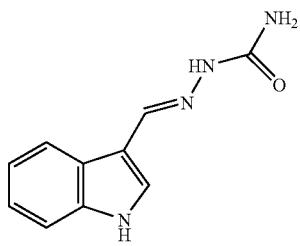

According to some embodiments, the methods of the invention involve administering a compound to a subject matter who is not otherwise indicated for treatment with the compound. Similarly, in some embodiments, the methods of the invention involve administering a pharmaceutical preparation to a subject who is not otherwise indicated for treatment with the pharmaceutical preparation. For example, in some embodiments, the methods involve treating patients who would not receive the compounds or pharmaceutical preparations recited herein for a condition other than a fungal infection.

According to another aspect of the invention, compositions of matter are provided. The compositions of matter comprise any compound embraced by Formula I, Formula II, Formula III, Formula IV, Formula V, and Formula VI, as well as every embodiment described above, as if specifically restated herein.

According to yet another aspect of the invention, pharmaceutical compositions are provided. The pharmaceutical compositions comprise a pharmaceutically acceptable carrier and any compound embraced by Formula I, Formula II, Formula III, Formula IV, Formula V, and Formula VI, as well as every embodiment described above, as if specifically restated herein.

In another aspect of the invention, kits are provided. The kits comprise any compound embraced by Formula I, Formula II, Formula III, Formula IV, Formula V, and Formula VI, as well as every embodiment described above, as if specifically restated herein, and instructions for use.

In some embodiments, the fungal infection is caused by a yeast of the *Candida* genus. In one embodiment, the yeast is of the *Candida albicans* species. In other embodiments, the *Candida* yeast may be of the *Candida dubliniensis, Candida parapsilosis, Candida tropicalis, Candida kefyr, Candida guilliermondii, Candida inconspicua, Candida famata, Candida glabrata, Candida krusei, Candida lusitaniae*, or other *Candida* species.

In all of the methods described for treating fungal infections, a subject in need of such treatment is administered one of the compounds described above in an amount effective to treat the fungal infection.

The subject is a human, non-human primate, or other mammal. In important embodiments, the subject is a human. In some embodiments, the subject is an HIV-positive patient. In other embodiments the subject is a non-human vertebrate selected from the group consisting of a dog, cat, horse, cow, pig, turkey, goat, fish, monkey, chicken, rat, mouse, and sheep.

In another aspect of the invention, methods for identifying modulators of phenotypic transition of *Candida* cells are provided. These methods include providing a sample of the cells in a first phenotypic form, adding a test compound to the sample of the cells, and observing whether or not there is a measurable change in the cells from a first phenotypic form to a second phenotypic form. The test compound is classified as a modulator of a phenotypic transition if there is a change or as not being a modulator of the phenotypic transition if there is no change in the cells. In important embodiments, the change is a morphological change. In some of these embodiments, the change is from a budded form to a hyphal form. In other embodiments, the change is from a budded form to a pseudohyphal form. In still other embodiments, the change is from a pseudohyphal form to a hyphal form. In yet other embodiments, the change may be a morphological change from a hyphal form to a budded form, a pseudohyphal form to a budded form, or even a hyphal form to a pseudohyphal form.

In some embodiments, the change is an increase in the amount of cells in the first phenotypic form compared to the amount of cells in the second phenotypic form. In other embodiments, the measurable change is a decrease in the amount of cells in the second phenotypic form.

In the methods for identifying modulators of phenotypic transitions described above, the *Candida* cells may be *Candida albicans* cells. However, these methods may also be applied to *Candida dubliniensis, Candida parapsilosis, Candida tropicalis, Candida kefyr, Candida guilliermondii, Candida inconspicua, Candida famata, Candida glabrata, Candida krusei, Candida lusitaniae*, and other species of *Candida* cells.

In another aspect of the invention, methods for identifying a modulator of a phenotypic transition of *S. cerevisiae* cells is provided. The method includes providing a sample of the cells characterized by a first phenotypic form, adding a test compound to the sample of the cells, and observing whether or not there is a measurable change in the cells from the first phenotypic form to a second phenotypic form. If there is a change, the test compound may be classified as a modulator, but if there is no change, the test compound may be classified as not being a modulator.

In one embodiment of the invention, methods for identifying inhibitors of the budded-to-hyphal transition of *Candida albicans* cells are provided. The method includes providing a sample of *Candida albicans* cells in the budded form, adding a test compound to the sample, and observing whether or not there is a measurable change from the budded form to the hyphal form. If there is no increase in the hyphal form, the test compound is classified as an inhibitor. If there is no change, the test compound is classified as not being an inhibitor.

Additionally, if there is a decrease in the budded form, the test compound is classified as an enhancer.

In another aspect of the invention, methods of studying the morphogenesis of organisms with actin-based morphogenesis using any of the modulators of the budded-to-hyphal transition described above are provided. In some embodiments, these organisms are eukaryotes. In some embodiments, these organisms are selected from *Drosophila melanogaster, Caenorhabditis elegans*, and *Arabidopsis thaliana*.

In any of the methods for identifying modulators of phenotypic transitions described above, there is optionally a step of determining if the test compound is substantially non-toxic to the subject cells. Test compounds that are substantially non-toxic to subject cells are preferred.

Each of the limitations of the invention can encompass various embodiments of the invention. Therefore, it is anticipated that each of the limitations of the invention involving any one element or combination of elements, can be included in each method.

Other aspects, features, and advantages of the present invention will become apparent from the following Detailed Description and Examples. It should be understood, however, that the Detailed Description and the specific Examples, while indicating the embodiments of the invention, are given by way of illustration only, since various changes and modifications within the spirit and the scope of the invention will become apparent to those skilled in the art from the Detailed Description.

BRIEF DESCRIPTION OF THE DRAWINGS

FIG. 3 illustrates results from a small molecule screen.

DETAILED DESCRIPTION OF THE INVENTION

Figure 1:
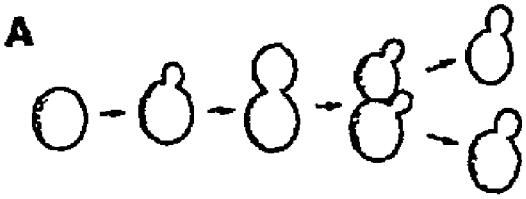
FIG. 1 illustrates the morphological status of *C. albicans*.
Figure 1:
Figure 1:
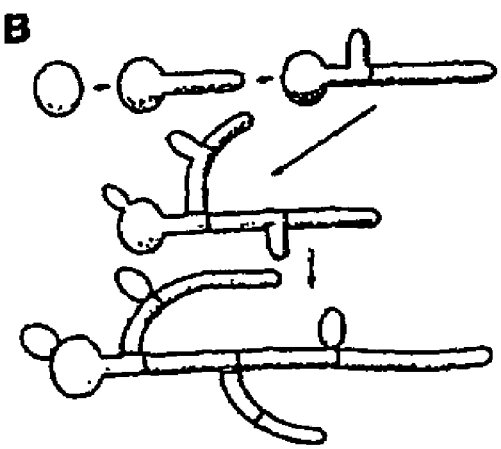
Figure 1:
Figure 1:
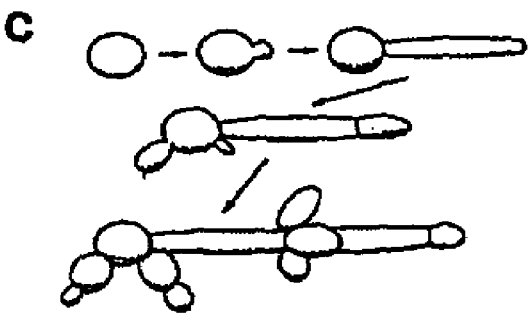
Figure 1:

The invention is based, in part, on the discovery of a method of identifying inhibitors of the budded-to-hyphal transition of yeast cells, and the use of the inhibitors to treat fungal infections. Previously, most, if not all, antifungal agents were designed to kill yeast cells, and often were toxic to the host (patient) cells as well.

Fungi are eucaryotic organisms, only a few of which cause infection in vertebrate mammals. Because fungi are eucaryotic organisms, they differ significantly from procaryotic bacteria in size, structural organization, life cycle and mechanism of multiplication. Fungi are classified generally based on morphological features, modes of reproduction and culture characteristics. Although fungi can cause different types of disease in subjects, such as respiratory allergies following inhalation of fungal antigens, fungal intoxication due to ingestion of toxic substances, such as amatatoxin and phallotoxin produced by poisonous mushrooms and aflotoxins, produced by *aspergillus* species, not all fungi cause infectious disease.

Infectious fungi can cause systemic or superficial infections. Primary systemic infection can occur in normal healthy subjects and opportunistic infections, are most frequently found in immuno-compromised subjects. The most common fungal agents causing primary systemic infection include *blastomyces, coccidioides*, and *histoplasma*. Common fungi causing opportunistic infection in immuno-compromised or immunosuppressed subjects include, but are not limited to, *candida albicans* (an organism which is normally part of the respiratory tract flora), *cryptococcus neoformans* (sometimes in normal flora of respiratory tract), and various *aspergillus* species. Systemic fungal infections are invasive infections of the internal organs. The organism usually enters the body through the lungs, gastrointestinal tract, or intravenous lines. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails. An example of a cutaneous infection is *Tinea* infections, such as ringworm, caused by *dermatophytes*, such as *microsporum* or *traicophyton* species, i.e., *microsporum canis, microsporum gypsum, tricofitin rubrum*.

Examples of fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* such as *Plasmodium falciparum, Plasmodium malariae, Plasmodium ovale*, and *Plasmodium vivax* and *Toxoplasma gondii*.

Diseases associated with fungal infection include aspergillosis, blastomycosis, candidiasis, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, penicilliosis, marneffeii, phaeohyphomycosis, rhinosporidioisis, sporotrichosis, and zygomycosis. The compounds of the invention are useful for treating diseases associated with fungal infection either alone or in combination with existing anti-fungal therapies.

Aspergillosis is a disease caused by the fungi of the genus *aspergillus*, which can lead to mild or severe disease, generally depending on factors such as the status of the host immune system. *Aspergillus* frequently arises as an opportunistic infection in patients having immune-suppressive diseases, or being treated with chemotherapy. Some forms of *aspergillus* can be treated with prednisone, disodium chromoglycat, nystatin, amphotericin B, itraconazole, or voriconazole.

Blastomycosis is a fungal infection arising from the organism *blastomyces dermatitis*. The infection initiates in the lungs and usually is disseminated to other body sites, especially the skin and bone. It is treated by amphotericin B, hydroxystilbamidine, itraconazole and voriconazole. When amphotericin B is used, at least 1.5 grams must be given to avoid relapse. However, if a drug is to be administered in combination with the compounds of the invention, lower doses may be given without a relapse. Generally hydroxystilbamidine has been used for treating the cutaneous form of the disease but not other forms. When combined with the compounds of the invention, it can also be used for the treatment of other forms, as well as in lower doses for the cutaneous form.

Candidiasis is a fungal infection caused by a member of the genus candida. The disease can be in the form of allergic, cutaneous, mucocutaneous, or systemic candidiasis. Nystatin is used for the treatment of the cutaneous, mucocutaneous, and allergic diseases. Amphotericin B is useful for treating this systemic disease. Other drugs useful for the treatment include 5-fluorocytosine, fluconazole, itraconazole and voriconazole.

Chromoblastomycosis is a chronic infection of the skin and subcutaneous tissue. Although the infection is usually localized, parts can disseminate systemically and in particular to the brain. Itraconazole and terbinafine are the drugs used to treat this infection. The principal fungi causing this infection are *cladophialophora, carrionii, fonsecaea, compacta, fonsecaea pedrosoi, phialophora, verruceosa, rhinocladiella, aquasbera*.

Coccidioidomycosis is a fungal disease of the respiratory tract which can be acute, chronic, severe or fatal. The disease is primarily caused by *coccidioides immitis*. Amphotericin B, itraconazole, fluconazole, ketaconazole, and voriconazole are anti-fungal agents that are used for the treatment of this disorder.

Cryptococcosis is a fungal disorder caused by *cryptococcus norformans* or *filobasidiella neoformans*. The disease can take the form of a chronic, subacute, acute, pulmonary, systemic, or meningitic disease, following primary infection in the lungs. If the disease spreads from the lungs to the central nervous system, it is usually treated immediately with amphotericin B and/or 5-fluorocytosine and in some cases fluconazole.

Fungal infections of the eye include mycotit keratitis, and endogenous or extension occulomycosis. Mycotic keratitis is caused by a variety of fungi including *acremonium, aspergillus, bipolaris, candida albicans, curvularia, exserohilum, fusarium*, and *lasiodiplodia*. Amphotericin B is not used for treatment because it irritates the infected tissue. Drugs useful for treating mycotit keratitis include pimaricin and fluconazole. Occulomycosis is generally caused by *candida albicans* or *rhizopus, arrhizus*. Amphotericin B is the anti-fungal agent used for treatment.

Fungal infections of the hair, nail, and skin include onychomycosis, piedra, pityrisis versizolor, tinea barbae, tinea capitis, tinea corporis, tinea cruris, tinea faosa, tinea nigra, tinea unguium. Onychomycosis, which is generally caused by fungi such as *acremonium, aspergillus, candida, fusarium, scopulariopisis, onychocola*, and *scytalidium*, can be treated with itraconazole, turbinifine, amphotericin B, gentian violet, resorcin, iodine, nystatin, thiabendazole, and glutarardehyde. Piedra, which is a colonization of the hair shaft to bifungal organisms such as *piedraia* and *trichosporin*, can be treated with keratolytic agents, mild fungicides, fluconazole, and itraconazole. The tineas are various forms of ringworm colonizing different bodily regions. These diseases are generally caused by fungi such as *microsporum, trichophyton*, and *epidermophyton*. The tineas can be treated with keratolytic agents, intraconazole, turbinifine, tolnaftate, chlotrimazole, miconazole, econazole, and ketaconzole.

Histoplasmosis (capsulati and duboisii) are fungal infections caused by *histoplasma* and *ajellomyces*. Histoplasmosis capsulati can adequately be treated with amphotericin B, itraconazole or voriconazole. If the subject being treated has AIDS, fluconazole is usually used. Histoplasmosis duboisii once it becomes disseminated, especially to the liver or spleen, is very difficult to treat. Amphotericin B, itraconazole, fluconazole, and voriconazole are used. When these compounds are combined with the compounds of the invention, prognosis may be improved.

Lobomycosis is a fungal infection caused by lacazia loboi. Lobomycosis is a cutaneous infection which develops into lesions which can be removed by surgery. There are not drugs specifically used for this disorder. Mycetoma is an infection caused by a variety of fungi including *eumycotic, acromonium, aspergillus, exophiala, leptosphaeria, madurella, neotestudina, pseudallesheria*, and *pyrenochieta*. The disease involves lesions of the cutaneous and subcutaneous tissues, which can rupture and spread to surrounding tissues. The mycetomas can be treated with ketoconazole, in combination with surgery.

Otomycosis is a fungal ear infection caused by *aspergillus* or *candida*. The infection is a superficial infection of the outer ear canal, which is characterized by inflammation, pruritus, scaling, and sever discomfort. It is a chronic recurring mycosis.

Paracoccidioidomycosis is a fungal infection cause by *paracoccidioides brasiliensis*. The disease originates as a pulmonary infection and can disseminate into the nasal, buccal, and gastrointestinal mucosa. Amphotericin B and sulfonamides are generally used to treat the disease.

Phaeohyphomycosis is a fungal infection caused by a variety of fungi including *cladophialophora, curvularia, bipolaris, exserohilum, exophiala, scedosporium, ochroconis, coniothyrium, phialophora, wangiella*, and *lasiodiplodia*. The infection can be localized or can invade various tissues including the brain, bone, eyes, and skin. Invasion of the brain or bone can be lethal. Generally, phaeohyphomycosis is treated with amphotericin B and phyfluorocytozine or intaconazole. Rhinosporidiosis is an infection of the mucus membrane caused by *rhinosporidium seeberi*. Local injection of amphotericin B is used as treatment.

Sporotrichosis is a chronic infection of the cutaneous tissues, subcutaneous tissues, or lymph system. The infection may also spread to tissues such as bone, muscle, CNS, lungs, and/or genitourinary system. Usually the fungi *sporothrix schenckii* is inhaled or passed through a lesion in the skin. Sporotrichosis is usually treated with oral potassium iodide, amphotericin B, or 5-fluorocytozine.

Zygomycosis is a chronic infection caused by *conidobolus* and *basidiobolus ranarum*. The disease is treated by potassium iodide and/or amphotericin B.

A compound that modulates phenotypic transitions of yeast cells is a compound that when added to a budded yeast causes transformation to a hyphal yeast. Preferred compounds are those set forth in the summary and functionally equivalent molecules thereof.

According to some aspects of the invention, the compounds used in the methods for treating fungal infections or in the methods for identifying modulators of yeast cell phenotypic transitions may exist in different isomeric forms. The compounds may be used in the methods of the invention as a substantially isomerically-pure compound, or as a mixture of isomers. Preferably, isomerically-pure compounds are used. Isomerically-pure, as used herein, means that one isomer will be present in an amount ranging from 51 to 100%, preferably, more than 80%, more preferably, more than 90%, even more preferably, more than 95%, and even more preferably, more than 99% pure with respect to the other isomer or isomers present, but not with respect to other impurities or compounds that may be present. Isomer, as used herein, may refer to an E or Z isomer, and R or S isomer, an enantiomer, a diastereomer, or, in the case of compounds with several diastereomers, a group of diastereomers, with respect to another group of diastereomers, which differ for example, with respect to just one stereocenter of the molecule.

Many of the compounds used in the methods described herein are available from commercial sources as pure compounds (for example, from ChemBridge, Corp., San Diego, Calif.). Others are not commercially available, but may be synthesized using commercially available starting materials and standard synthetic chemistry techniques using no more than routine skill in the art.

In another aspect of the invention, methods for identifying modulators of morphological transitions are provided. These methods (or assays) are based, in part, on the discovery that certain molecules have an inhibitory effect on the budded-to-hyphal transition of *Candida albicans* cells. In addition, the methods may be useful to understand the cellular and molecular mechanisms of yeast and other cells.

The methods for identifying modulators of phenotypic transitions include providing a sample of cells characterized by a phenotypic form. A phenotypic form is an observable state. Morphological forms are one type of phenotypic form. Phenotypic forms may be an observable state of a cell or collection of cells, such as a budded form, a hyphal form, a pseudohyphal form, and the like. A measurable change from one phenotypic form to another is a directly or indirectly observable phenotypic transition, such as the change of a cell or collection of cells from one phenotypic form to another, the formation of intracellular structure, the formation of extracellular structure, the inhibition or enhancement of a cellular process which results in a measurable change downstream. Specific examples include the formation of pedestals on cells, the formation of mitotic spindles within cells, cell differentiation, centrosome duplication, actin assembly, and cell surface receptor activation (for a review, see Ward, G. E., et al., 2002, Cellular Microbio. 4(8): 471-482). In one embodiment, the phenotypic transition observed is a morphological transition between a cellular budded form, a cellular hyphal form, and/or a cellular pseudohyphal form.

The methods for identifying modulators of phenotypic transitions include providing a test compound to a cell or a sample of cells. A test compound, as used herein, is a compound that is added to the cell or cells to query whether or not it is capable of inducing a phenotypic transition. Test compounds may be inhibitors or enhancers (activators) of a phenotypic transition, or may have no effect. Often test compounds are agonists or antagonists of certain cellular transitions which include or lead to phenotypic transitions. Test compounds may be added to cell(s) individually, though often a library approach is used to increase the amount of test compounds that can be screened for activity in a given amount of time. High throughput screening methods are often employed as well.

The test compounds are optionally assayed for toxicity against the subject cells. In one embodiment, the toxicity of a test compound against human cells is determined. A step of selecting test compounds that are substantially non-toxic to subject cells is provided. "Substantially non-toxic" means that the test compound can be administered to a subject with an acceptable amount of damage to the host (subject's) cells. An acceptable amount of damage can be determined by one of skill in the art with no more than routine skill. Acceptable amounts may depend on route of administration, risk of side effects versus benefit of administration, etc.

In addition to the powerful assay to identify yeast form modulators, understanding the input signals and output responses that lead to the budded-to-hyphal transition will lead to insight into virulence mechanisms and may ultimately lead to new anti-fungal therapeutic targets and drugs. New anti-fungal therapeutic targets and drugs are needed because there are serious side effects due to renal and liver dysfunction associated with the polyenes (e.g., amphotericin B, nystatin) that are usually used to treat *C. albicans* infections. In addition, a significant increase in resistance to the less toxic azole drugs (e.g., fluconoazole) has occurred within the patient population, especially HIV-positive patients (reviewed in White, T. C., et al., 1998, Clin. Microbiol. Rev. 11: 382-402).

*C. albicans* can exist in different morphological states including budded or yeast-like cells and hyphal forms. FIG. 1 illustrates the morphological states of *C. albicans*, including the budded or yeast-like (A), pseudohyphal (B), and hyphal growth forms.

The morphological states of *C. albicans* include round to ovoid budded or yeast-like cells and filamentous forms including pseudohyphae (chains of ellipsoidal cells with constricted septa between mother and daughter cells) and hyphae (long filaments with no constriction at septa). Hyphal cells are morphologically distinct from budded and pseudohyphal cells, with differences in septation patterns, actin dynamics, and growth properties. Hyphal growth is the result of alterations in polarized growth patterns and in transit through the cell cycle. The budded-to-hyphal transition occurs in response to environmental stress signals such as temperature above 35° C., pH above 6.5, nitrogen and/or carbon starvation, low oxygen concentration, and changes in cell density, growth in serum or other chemicals such as N-acetylglucosamine, proline and other amino acids, or alcohols, and the presence of host macrophages (Brown, A. J. P., 2002. p. 87-93. In R. A. Calderone (ed.), *Candida* and Candidiasis. ASM Press, Washington, D.C.). In response to these hyphal-inducing signals, the expression of a variety of hyphal-specific genes increases, including genes that encode cell surface adhesins and secreted proteinases. Induced genes ALS3, ALS8, and HWP1 (adhesins), HYR1 (cell surface glycoprotein), SAP4, SAP5, SAP 6 (secreted aspartyl proteinases), and ECE1 (unknown function) are believed to be important reporters for examining the effects of the Cdc42p signaling pathway on the budded-to-hyphal transition.

The pathogenicity of *C. albicans* can be attributed to its ability to survive and thrive in multiple microenvironments within a host, including multiple organs, the mucosa, and the bloodstream, as well as to virulence factors that aid in the adherence and invasion of multiple cell types (Brown, A. J. P., et al., 1999. Trends Microbiol. 7: 333-338; Mitchell, A. P. 1998, Curr. Opin. Microbiol. 1: 687-692; Odds, F. C. 1994, J. Am. Acad. Dermatol. 31: S2-S5). *C. albicans* exists within immunocompetent individuals in a commensal relationship on mucosal linings of the oral cavity, esophagus, vagina, gastrointestinal tract, etc. Oropharyngeal, esophageal, vulvovaginal, and cutaneous candidiasis leads to significant morbidity. Lethality is often associated with systemic infections in immunocompromised patients. Systemic infections arise from colonization of mucosal surfaces by adherence to epithelial cells, followed by the penetration of epithelial and endothelial cell barriers and dissemination throughout the body (Filler, S. G., et al., 1995, Infect. Immun. 63: 976-983).

It is believed that the vascular endothelium has a key role in the dissemination of *C. albicans* which leads to establishment of systemic candidiasis. Endothelial cells are sensitive to invasion and damage by *C. albicans*, which requires the attachment of germinated *C. albicans* to the endothelial cells, their phagocytosis, and induction of hyphal-specific genes. This damage can be mitigated by *C. albicans* strains with mutations in the proteinase Sap2p (Ibrahim, A. S., et al., 1998, Infect. Immun. 66: 3003-3005) and the adhesin Hwp1p Tsuchimori, N., et al., 2000, Infect. Immun. 68: 1997-2002). Both budded and hyphal forms of *C. albicans* have been identified in infections and are important for virulence. The budded form is found predominantly attached to epithelial cells and the hyphal form is found disseminated, presumably due to its enhanced ability to invade cells through the production and secretion of proteinases and hydrolases.

Figure 2:
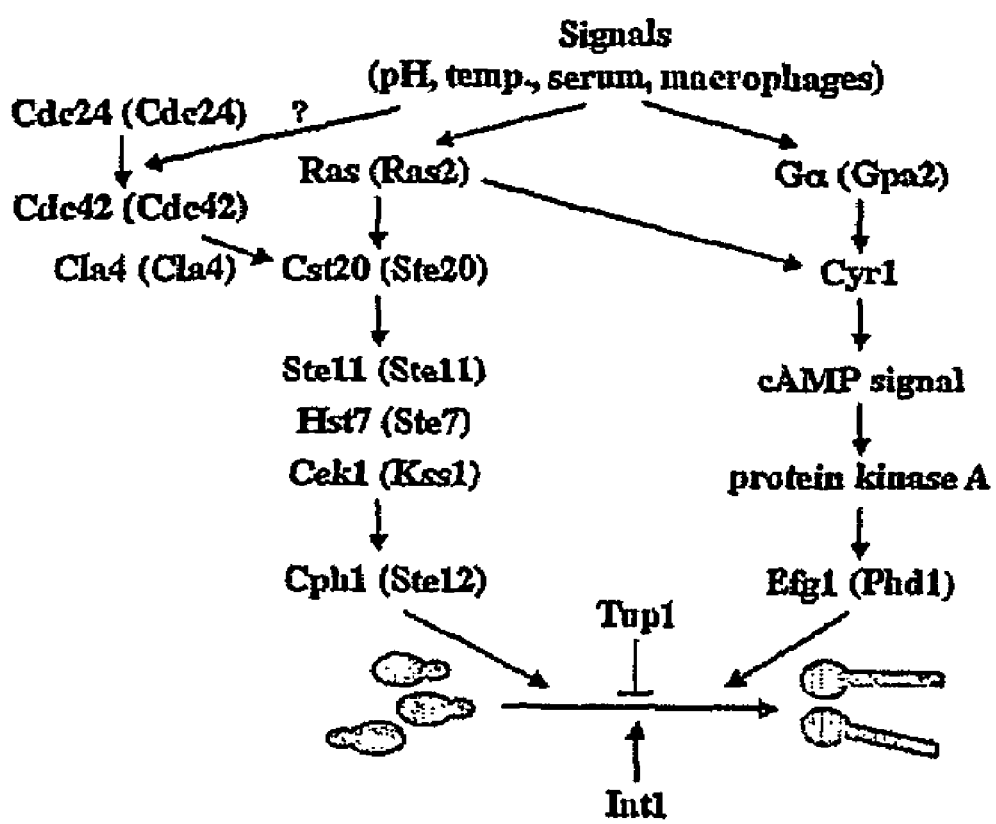
FIG. 2 illustrates the cell signaling pathways of *C. albicans*.

Since *C. albicans* cells respond to a variety of different growth and environmental signals to induce the budded-to-hyphal transition, it is believed that multiple signaling pathways function in hyphal development, shown in FIG. 2 (Brown, A. J. P. 2002. p. 95-106. In R. A. Calderone (ed.), *Candida* and Candidiasis. ASM Press, Washington, D.C). Mutational analyses indicate that the Tup1p, Cph1p, and Efg1p transcriptional regulatory proteins function independently in promoting (Cph1p and Efg1p) or inhibiting (Tup1p) hyphal development (Braun, B. R., et al., 2000, Genetics 155:

57-67). The Cst20p-Hst7p-Cek1p MAP kinase pathway, which is homologous to the Ste20p-Ste7p-Kss1p pathway in *S. cerevisiae*, signals to the Cph1p transcription factor (*S. cerevisiae* Ste12p) to induce hyphal-specific genes (Csank, C., et al, 1998, Infect. Immun. 66: 2713-2721; Köhler, J. R., et al., 1996, Proc. Natl. Acad. Sci. USA 93: 13223-13228; Leberer, E., et al., 1996, Proc. Natl. Acad. Sci. USA 93: 13217-13222; Liu, H., et al., 1994, Science 266: 1723-1726). Two Cdc42p-interacting proteins, the p21-activated kinase (PAK) CaCla4p and a phosphatidylinositol 3-kinase CaVps34p, are also involved in hyphal development (Bruckmann, et al. 2000. Microbiol.-UK 146: 2755-2764; Leberer, E., et al., 1997, Curr. Biol. 7:539-546). In a parallel pathway, the Efg1p transcription factor functions downstream of Tpk2p, the catalytic component of protein Icinase A, and the Ras GTPase to integrate a cAMP signal into hyphal development (Feng, Q. H., et al., 1999, J Bacteriol 181: 6339-6346; Lo, H. J., et al., 1997, Cell 90: 939-949; Sonneborn, A., et al., 2000, Mol. Microbiol. 35: 386-396; Stoldt, V. R., et al., 1997, EMBO J. 16: 1982-1991). Recently, the Cos1p/Nik1p two-component histidine kinase (Alex, et al., 1998. Proc. Natl. Acad. Sci. USA 95: 7069-7073; Nagahashi, S., et al. 1998, Microbiol. 144: 425-432; Srikantha, T., et al., 1998, Microbiol. 144: 2715-2729), a Hog1p MAP kinase (Monge, R. A., et al., 1999, J. Bacteriol. 181: 3058-3068), and the Crk1p cyclin-dependent kinase (Chen, et al., 2000, Mol. Cell. Biol. 20: 8696-8708) have also been shown to be involved in hyphal development. It is believed that these different signaling pathways are activated by separate but overlapping environmental signals, eventually leading to rearrangements of the actin- and tubulin-based cytoskeleton (Akashi, et al., 1994. Microbiol. 140: 271-280; Yokoyama, K., et al., 1994, Microbiol. 140: 281-287). For example, the Efg1p pathway can be triggered by pH, N-acetylglucosamine, proline, and nitrogen and/or carbon starvation while the Cph1p pathway can be stimulated by nitrogen starvation but not in response to N-acetylglucosamine, amino acids, or serum (Brown, A. J. P., 2002. p. 95-106. In R. A. Calderone (ed.), *Candida* and Candidiasis. ASM Press, Washington, D.C.). In addition, the hyphal-specific genes ALS8, ECE1, HWP1, and HYR1 are regulated primarily by the Efg1p pathway with the Cph1p pathway being less important (Braun, B. R., et al., 2000. Genetics 155: 57-67; Brown, A. J. P. 2002. p. 95-106. In R. A. Calderone (ed.), *Candida* and Candidiasis. ASM Press, Washington, D.C.). However, the molecular mechanisms that underlie these different signaling pathways and their potential cross-talk are still unclear.

To identify molecules that stimulate the budded-to-hyphal transition, cells are incubated in the absence of Spider media; stimulatory molecules are identified by rapidly screening a picture of each well for the presence of hyphae in the absence of added Spider media. Secondary screens with stimulatory molecules are carried out as described below.

The structure of the inhibitory molecules identified are used to search molecule libraries to identify structurally related molecules. The use of chemical libraries for screening is known (see, for example, Ward, G. E., et al., 2002, Cellular Microbio. 4(8): 471-482). Chemical libraries are readily available from numerous sources, such as Chemical Diversity (San Diego, Calif.), NeoGenesis (Cambridge, Mass.), and Chembank (National Cancer Institute). Derivatives of the inhibitors (similar molecules to the inhibitors) are also designed using the inhibitors. These related molecules are tested for their effects in the assay, which allows for identification of key structures of the bioactive molecules that are required for biological activity as well as to identify related molecules that may have better efficacy (e.g., show effects at a lower dose). These more efficient bioactive molecules for each of the sets of related molecules identified from the database searches are further analyzed for structural similarity to known anti-fungal compounds and for phenotypes in secondary assays (as described below).

Inhibitory or stimulatory bioactive compounds identified in this screen are likely to function through a diverse set of mechanisms. As a first step in deciphering these mechanisms, the effects of these molecules under different hyphal-inducing conditions are tested. Subsequently, several secondary screens are performed to identify the cellular processes impacted by these molecules. As mentioned above, Hyphae can be induced in response to a variety of environmental stimuli that act through different signaling pathways. Molecules that affect the budded-to-hyphal transition on Spider media in the screen may or may not affect the transition in response to other stimuli such as changes in pH, nitrogen and/or carbon starvation, growth in N-acetylglucosamine growth in proline, or growth in serum. Therefore, the molecules are tested for inhibitory or stimulatory effects under these growth conditions using standard protocols. The effects of these molecules under different hyphal-inducing conditions may provide clues to the signaling pathways impacted by the molecules.

In the methods for treating fungal infections provided herein, the compounds described above are administered in effective amounts. An effective amount means that amount necessary to delay the onset of, inhibit the progression of, halt altogether the onset or progression of, or diagnose the particular infection being treated. When administered to a subject, effective amounts will depend on the particular condition being treated, the severity of the condition, individual patient parameters including age, physical condition, size and weight, concurrent treatment, frequency of treatment, and the mode of administration. These factors are well known to those of ordinary skill in the art and can be addressed with no more than routine experimentation. It is preferred generally that a maximum dose be used, that is, the highest safe dose according to some medical judgment.

As used herein, the term treat, treated, or treating when used with respect to an disorder such as an infectious disease refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

Generally, daily doses of active compounds will be from about 0.01 milligrams/kg per day to 1000 milligrams/kg per day. It is expected that oral doses in the range of 0.5 to 50 milligrams/kg, or even 1-10 milligrams/kg per day, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. It is expected that intravenous and other parenteral forms of administration will yield the desired results in the range of 0.1 to 10 milligrams/kg per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-2-naphthalenecarboxylic, and benzene sulfonic. Also, pharmaceutically acceptable salts can be prepared as alkaline metal or alkaline earth salts, such as sodium, ammonium, magnesium, potassium or calcium salts of the carboxylic acid group.

Suitable buffering agents include: acetic acid and salts thereof (1-2% W/V); citric acid and salts thereof (1-3% W/V); boric acid and salts thereof (0.5-2.5% W/V); and phosphoric acid and salts thereof (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

A variety of administration routes are available. The particular mode selected will depend, of course, upon the particular combination of drugs selected, the severity of the condition or disorder being treated, or prevented, the condition of the patient, and the dosage required for therapeutic efficacy. The methods of this invention, generally spealing, may be practiced using any mode of administration that is medically acceptable, meaning any mode that produces effective levels of the active compounds without causing clinically unacceptable adverse effects. Such modes of administration include oral, rectal, topical, transdermal, sublingual or intramuscular, infusion, intraparenteral, intravenous, intramuscular, intracavity, as a feed additive, as an aerosol, aurally (e.g., via eardrops), intranasal, inhalation, or subcutaneous. Direct injection could also be preferred for local delivery to the site of infection. Oral administration may be preferred for prophylactic treatment because of the convenience of the subject (patient) as well as the dosing schedule.

For oral administration, the compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4: 185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds. The compound of the invention is delivered to the lungs of a mammal while inhaling and traverses across the lung epithelial lining to the blood stream. Examples of reports of inhaled molecules include Adjei et al., 1990, Pharmaceutical Research, 7: 565-569; Adjei et al., 1990, International Journal of Pharmaceutics, 63: 135-144 (leuprolide acetate); Braquet et al., 1989, Journal of Cardiovascular Pharmacology, 13(suppl. 5): 143-146 (endothelin-1); Hubbard et al., 1989, Annals of Internal Medicine, Vol. III, pp. 206-212 (a1-antitrypsin); Smith et al., 1989, J. Clin. Invest. 84: 1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140: 3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compounds of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compounds may also be prepared in different formulations depending on the type of chemical modification or the type of device employed.

Formulations suitable for use with a nebulizer, either jet or ultrasonic, will typically comprise the compound dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., 50 to 90% by weight of the formulation. The compound of the invention should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249: 1527-1533, 1990, which is incorporated herein by reference.

The compositions may conveniently be presented in unit dosage form and may be prepared by any of the methods well known in the art of pharmacy. All methods include the step of bringing the compounds of the invention into association with a carrier which constitutes one or more accessory ingredients. In general, the compositions are prepared by uniformly and intimately bringing the compounds of the invention into association with a liquid carrier, a finely divided solid carrier, or both, and then, if necessary, shaping the product.

Other delivery systems can include time-release, delayed release or sustained release delivery systems. Such systems can avoid repeated administrations of the compounds of the invention, increasing convenience to the subject and the physician. Many types of release delivery systems are available and known to those of ordinary skill in the art. They include polymer based systems such as polylactic and polyglycolic acid, polyanhydrides and polycaprolactone, nonpolymer systems that are lipids including sterols such as cholesterol, liposomes; phospholipids; hydrogel release systems; silastic systems; peptide based system; implants and the like. Specific examples include, but are not limited to: (a) erosional systems in which the active agent is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hard wired delivery systems can be used, some of which are adapted for implantation.

Use of a long-term sustained release implant may be particularly suitable for treatment of chronic conditions.

"Long-term" release, as used herein, means that the implant is constructed and arranged to deliver therapeutic levels of the active ingredient for at least 7 days, and preferably 30-60 days. The implant may be positioned at the site of infection. Long-term sustained release implants are well-known to those of ordinary skill in the art and include some of the release systems described above.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of fungal infections. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, and functionally equivalent compositions thereof, but can also include a composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules and/or particles as described. The kits also may contain instructions for mixing, diluting, and/or administrating the compounds. The kits also can include other containers with one or more solvents, surfactants, preservative and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

The compounds of the invention may optionally be delivered with other antifungal agents in the form of antifungal cocktails, or individually, yet close enough in time to have a synergistic effect on the treatment of the infection. An antifungal cocktail is a mixture of any one of the above-described compounds with another antifungal drug which may or may not be a compound of the invention. The use of such cocktails in pharmaceutical preparations is routine. In this embodiment, a common administration vehicle (e.g., tablet, implants, injectable solution, injectable liposome solution, etc.) could contain both the compound of the invention and the other antifungal agent(s).

Anti-fungal agents are useful for the treatment and prevention of infective fungi. Some of these treatments are described above. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Antifungal agents include Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Cancidas (Caspofungin Acetate), Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

Each of the references, patents, and patent applications referred to herein is hereby incorporated by reference.

EXAMPLES

Example 1

New High-Throughput Screen for Inhibitors and Enhancers of the Budded-to-Hyphal Transition

*C. albicans* is a constitutively diploid organism and, thus, standard sexual genetic approaches for the isolation of recessive, loss-of-function mutants are not currently feasible. Therefore, alternative strategies for the identification of components participating in the budded-to-hyphal transition are employed.

One such approach is a high-throughput small molecule screen, in which a large diverse collection of individual small organic molecules (<1500 Da) are tested for their ability to inhibit or enhance a biological process, in this case the budded-to-hyphal transition. The active molecules and their structural derivatives are used to identify the component or components involved in the process. This "phenotype-based" approach has been used successfully to identify novel components involved in a variety of different biological processes (reviewed in Ward, G. E., et al., 2002, Cell. Microbiol. 4: 471-482).

A small molecule screen was developed to identify inhibitors and enhancers of the budded-to-hyphal transition. A proof-of-concept study verified that the assay is robust and reproducible. In addition, several known and new molecules that inhibit the budded-to-hyphal transition were identified.

For the screen, *C. albicans* cells were grown in YNB media that inhibits hyphal growth and then transferred to 384-well optical plates containing Spider media to induce the budded-to-hyphal transition and hyphal elongation. Microscopic examination indicated that *C. albicans* cells reproducibly undergo the budded-to-hyphal transition and show significant hyphal elongation within 4 hours (h) at 37° C. in Spider media shown FIG. 3. In FIG. 3, the indicated small molecules were added at the indicated concentrations at time 0 and growth was allowed to continue for 4 h at 37° C. before the cells were fixed and observed microscopically. YNB media is well known in the art and contains yeast nitrogen base (DIFCO Labs.), glucose (US Biological) and d-H$_2$O. Spyder media is well known in the art and contains nutrient broth (DIFCO Labs.), mannitol (Sigma-Aldrich), K$_2$HPO$_4$ (Sigma-Aldrich) and d-H$_2$O.

Next, small molecules were assayed for their ability to inhibit the Spider media-induced hyphal growth. As a proof-of-concept experiment, latrunculin-A (Lat A) was added, which reversibly inhibits yeast growth by depolymerizing actin. Addition of 1.6 μM Lat A inhibited the budded-to-hyphal transition and hyphal growth. This inhibition was both dose-dependent (effect was lost at 0.1 μM) and reversible. This result indicated that the screen was sensitive to a known cytostatic drug.

Using this strategy, 70 molecules were screened from a Chembridge small molecule library (ChemBridge Corp., San Diego, Calif.). Of the 70 molecules, most had no effect on hyphal formation, several were either cytostatic or cytotoxic leading to lack of growth of budded or hyphal cells, and some inhibited the budded-to-hyphal transition and hyphal elongation without affecting budded growth. The inhibitory molecules include the following compounds:

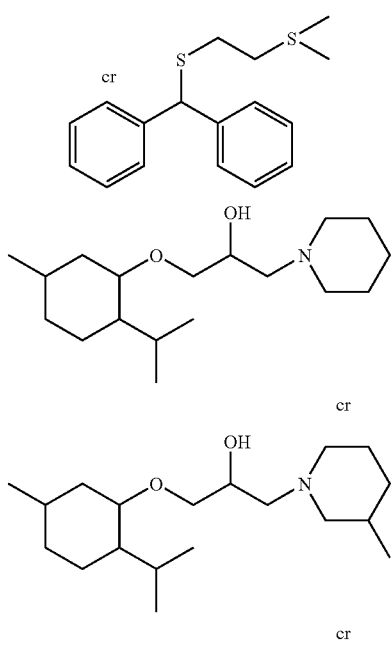

-continued

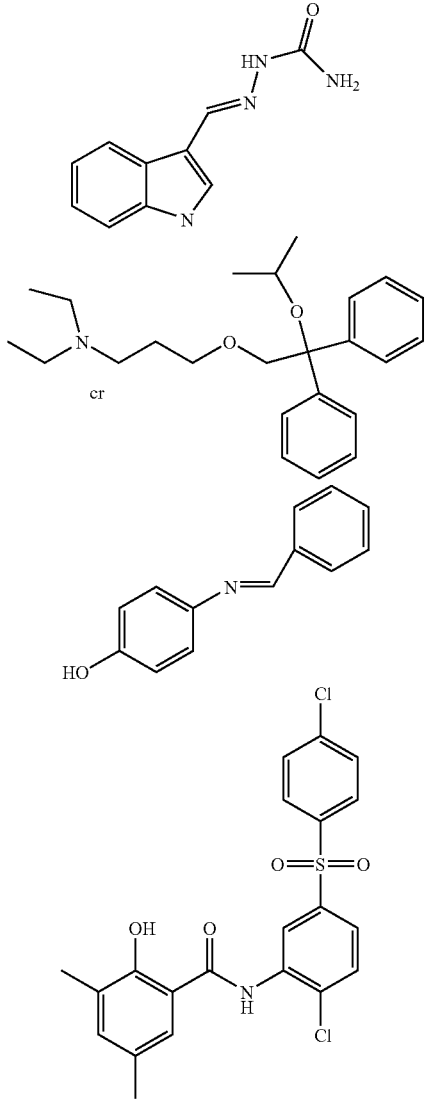

Interestingly, a known actin-stabilizing drug jasplakinolide (Jas) was identified as a dose-dependent cytotoxic molecule in the screen, leading to an apparent cell-cycle arrest as small budded cells (shown in FIG. 3). Jasplakinolide was previously shown to have anti-fungal activity (Scott, V. R., et al., 1988, Antimicrob. Agents Chemother. 32: 1154-1157), and its isolation from a random selection of small molecules further supports the efficacy of the screen. The effects of the active molecules that inhibited the budded-to-hyphal transition were also shown to be dose-dependent and reversible, indicating that the inability to undergo the budded-to-hyphal transition was not due to a cytotoxic effect.

Molecules from the Chembridge library that are structurally related to the active molecules were also assayed for their efficacy.

These results indicate that the screen is robust, reproducible, amenable to high-throughput protocols, and able to identify known and novel molecules that can inhibit the budded-to-hyphal transition. This approach significantly augments the genetic and biochemical strategies currently used to identify and characterize the components that regulate the budded-to-hyphal transition and enhance the identification of potential therapeutic molecules.

Example 2

Identification of New Components of the Budded-to-Hyphal Transition Pathway Using a New High-Throughput Small Molecule Screen While typical genetic approaches are relatively facile with modern techniques, the use of genetic screens to identify new components of the budded-to-hyphal transition pathway is complicated by the fact that *C. albicans* is a constitutive diploid. Certain *C. albicans* isolates have been shown recently to mate under laboratory conditions at a reasonable frequency to form tetraploids (Miller, M. G., et al., 2002, Cell 110: 293-302). However, these tetraploids do not undergo a demonstrated meiosis or meiotic recombination, making classical sexual genetic approaches difficult. In order to circumvent this limitation, a "forward chemical genetic" approach was developed to identify small molecules that either inhibit or stimulate the budded-to-hyphal transition, described below.

Several molecules that inhibit the budded-to-hyphal transition have been identified, including:

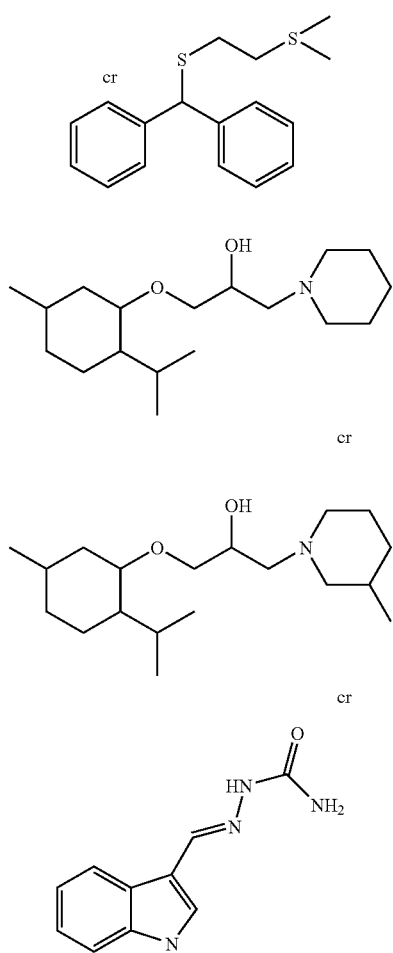

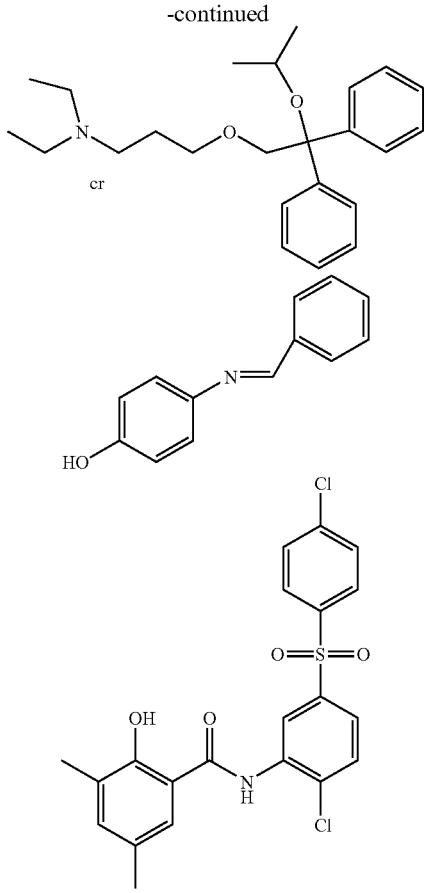

-continued

These molecules were further characterized in secondary screens for their ability to inhibit hyphal induction under the variety of hyphal-inducing signals described previously and for effects on specific cell biological processes or structures (described below). In addition, these molecules are used as reagents to identify their cellular targets and their cognate pathways. Additional molecules are also identified using similar techniques and in a high-throughput version of the screen. Not only does this approach allow the dissection of the budded-to-hyphal transition pathway, but may also lead to new therapeutic molecules and targets.

The basic microscopic screen was described in detail above. To identify inhibitors, *C. albicans* cells are initially grown in YNB media that inhibits hyphal growth and then transferred to 384-well optical assay plates containing Spider media to induce the transition to hyphae. Individual molecules from the Chembridge small molecule library (Kao, R. Y. T., et al., 2002, Proc. Natl. Acad. Sci. USA 99: 10066-10071), or other library, are transferred from a 384-well plate containing stock solutions to individual wells of the assay plates. For convenience, positive and negative controls may be located at each corner of the plate. These plates are incubated at 37° C. for 4 h to allow for hyphal elongation before the cells are fixed and screened. Screening occurs on an inverted Nikon microscope with a computer driven XY stage with DIC/Hoffman optics, digital SPOT® camera and automatic shutter. Pictures are automatically taken of each well with the plate number and well position embedded in the picture through a script written for OpenLab® image analysis software from Improvision (INVIVO, from QED Imaging, Inc.). Inhibitory molecules are identified by rapidly screening a picture of each well for the presence of budded cells and absence of hyphal cells. Each inhibitor is retested at both 4 h and 16 h to eliminate those compounds that are cytotoxic, delay hyphal formation, or delay elongation through a growth defect. Molecules that give consistent inhibition of the budded-to-hyphal transition with continued budded growth with no hyphae out to 16 are further characterized as described below. A dose-response for each molecule is established through serial dilutions in order to determine the threshold concentration of each molecule. Typical threshold concentrations range from about 1 to about 100 micromolar (μM). In addition, the reversibility of each molecule is tested by washing out the molecule and adding fresh Spider media; cells that resume hyphal growth indicate that the molecule is reversible in action and that the molecule's initial effects were not due to cytotoxicity.

What is claimed is:

1. A method for treating a fungal infection in a subject selected from human and non-human vertebrate in need of such treatment comprising administering to the subject a compound of the formula:

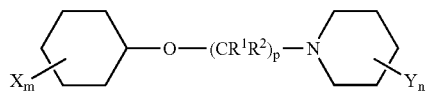

or a pharmaceutically acceptable salt thereof,
wherein $R^1$ and $R^2$ are independently selected from the group consisting of hydrogen, $C_1$-$C_6$ alkyl, $C_1$-$C_6$ alkoxy, hydroxy, and halo;
p is an integer ranging from 1 to 5;
each X and each Y are independently selected from the group consisting of halo, hydroxy, nitro, $C_1$-$C_6$ alkoxy, $C_1$-$C_6$ alkyl, $C_1$-$C_6$ alkenyl, $C_1$-$C_6$ alkynyl, amido, aryl, heteroaryl, and acyl; or two Xs or two Ys together form a 5, 6, or 7-membered ring;
m is an integer varying from 0 to 5; and
n is an integer varying from 0 to 5;
in an amount effective to treat the fungal infection, wherein the fungal infection is caused by a yeast of the *Candida* genus.

2. The method of claim 1 wherein the compound is administered in combination with a second antifungal agent.

3. The method of claim 1, wherein the compound is of the formula:

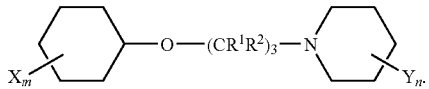

4. The method of claim 3, wherein m is an integer varying from 2 to 5.

5. The method of claim 3, wherein the compound is of the formula:

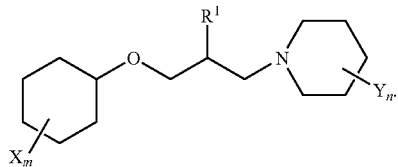

6. The method of claim 5, wherein the compound is of the formula:

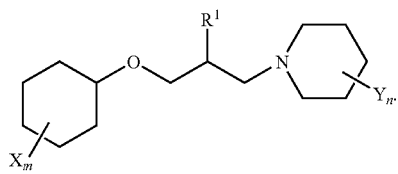

7. The method of claim 6, wherein X and Y are each $C_1$-$C_6$ alkyl.

8. The method of claim 1, wherein the compound is greater than 90% of one diastereomer.

9. The method of claim 7, wherein the compound is of the formula:

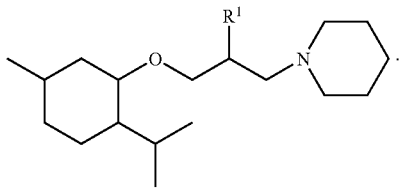

10. The method of claim 9, wherein the compound is greater than 90% of one diastereomer.

11. The method of claim 7, wherein the compound is of the formula:

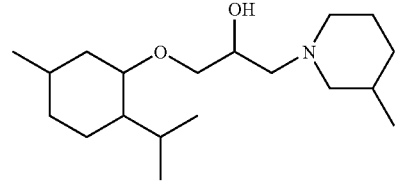

12. The method of claim 11, wherein the compound is greater than 90% of one diastereomer.

13. The method of claim 1, wherein the fungal infection is caused by *Candida albicans*.

* * * * *

UNITED STATES PATENT AND TRADEMARK OFFICE
CERTIFICATE OF CORRECTION

PATENT NO. : 7,763,660 B2
APPLICATION NO. : 10/544691
DATED : July 27, 2010
INVENTOR(S) : Douglas I. Johnson et al.

It is certified that error appears in the above-identified patent and that said Letters Patent is hereby corrected as shown below:

In Column 7, line 48, "Formula II." should read --Formula II,--.

In Column 8, line 2, "*Candida kerfyr*" should read --*Candida kefyr*--.

In Column 15, line 15, "Icinase" should read --kinase--.

In Column 17, line 32, "spealing" should read --speaking--.

Line 23, In Column 30, Claim 7, "arc" should read --are--.

Signed and Sealed this

Thirtieth Day of November, 2010

David J. Kappos
*Director of the United States Patent and Trademark Office*